United States Patent [19]

Rentzea et al.

[11] Patent Number: 4,708,960
[45] Date of Patent: Nov. 24, 1987

[54] N-(ARYLPROPYL)-AZOLYLUREAS, AND FUNGICIDES CONTAINING THESE COMPOUNDS

[75] Inventors: Costin Rentzea, Heidelberg; Ernst Buschmann, Ludwigshafen; Walter Himmele, Walldorf; Eberhard Ammermann, Ludwigshafen; Ernst-Heinrich Pommer, Limburgerhof, all of Fed. Rep. of Germany

[73] Assignee: BASF Aktiengesellschaft, Ludwigshafen, Fed. Rep. of Germany

[21] Appl. No.: 724,585

[22] Filed: Apr. 18, 1985

[30] Foreign Application Priority Data

Apr. 21, 1984 [DE] Fed. Rep. of Germany ....... 3415139

[51] Int. Cl.$^4$ .................. A01N 43/50; A01N 43/653; C07D 233/60; C07D 249/14
[52] U.S. Cl. ................................. 514/383; 514/399; 548/262; 548/341
[58] Field of Search ................ 548/262, 341; 514/383, 514/399

[56] References Cited

U.S. PATENT DOCUMENTS 3,991,071 11/1976 Brookes et al. .................... 548/341
4,046,773 9/1977 Andriska et al. .................... 548/339

FOREIGN PATENT DOCUMENTS 1136342 9/1962 Fed. Rep. of Germany .
1469772 4/1977 United Kingdom .
2011414 7/1979 United Kingdom .

OTHER PUBLICATIONS

Chemical Week, Jun. 21, 1972, pp. 63 and 46.

Primary Examiner—Richard L. Raymond
Attorney, Agent, or Firm—Keil & Weinkauf

[57] ABSTRACT

N-(Arylpropyl)-azolylureas of the formula

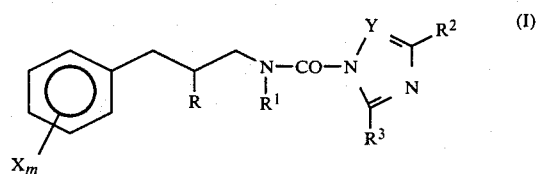

where R is alkyl, X is hydrogen, halogen, nitro, cyano, trifluoromethyl, alkyl, alkoxy, alkylthio, phenyl or phenoxy, m is an integer from 1 to 4, Y is CH or N, $R^1$ is alkyl, alkenyl, alkoxyalkyl, alkylthioalkyl, cycloalkyl or cycloalkylalkyl or an unsubstituted or substituted phenyl or benzyl radical, and $R^2$ and $R^3$ are each hydrogen or alkyl, and fungicides which contain these compounds.

4 Claims, No Drawings

N-(ARYLPROPYL)-AZOLYLUREAS, AND FUNGICIDES CONTAINING THESE COMPOUNDS

The present invention relates to novel N-(arylpropyl)-azolylureas, processes for their preparation, and fungicides which contain these compounds as active ingredients.

It has been disclosed that N-trichloromethylthiotetrahydrophthalimide and N-trichloromethylthiophthalimide can be used as fungicides in agriculture as well as in fruit cultivation and horticulture (Chemical Week, 1972, June 21, pages 46 and 63). However, the conventional agents can be used only before infection, and their actions do not meet practical requirements at low application rates.

We have found that N-(arylpropyl)-azolylureas of the formula

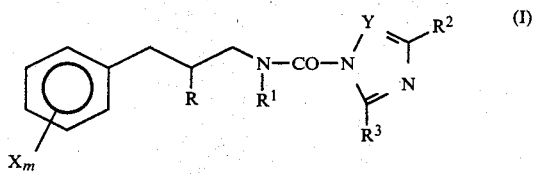

where R is alkyl of 1 to 4 carbon atoms, X is hydrogen, halogen, nitro, cyano, trifluoromethyl or alkyl, alkoxy or alkylthio, each of which is of 1 to 6 carbon atoms, or phenyl or phenoxy, m is an integer from 1 to 4, the individual groups X being identical or different when m is greater than 1, Y is CH or N, $R^1$ is alkyl, alkenyl, alkoxyalkyl, alkylthioalkyl, cycloalkyl or cycloalkylalkyl, each of not more than 12 carbon atoms, or is phenyl or benzyl, each of which is unsubstituted or substituted by halogen, $C_1$-$C_4$-alkyl, $C_1$-$C_4$-alkoxy, trifluoromethyl, nitro or cyano, and $R^2$ and $R^3$ are identical or different and are each hydrogen or alkyl of 1 to 5 carbon atoms, are very effective against harmful fungi.

The novel compounds of the formula I contain chiral centers and are generally obtained in the form of racemates or diastereomer mixtures. For some of the novel compounds, the diastereomers can be separated, for example by column chromatography, or can be isolated in pure form on the basis of solubility differences. Pure enantiomers can be obtained from such pure diastereomers by a conventional method. The mixtures and the pure compounds are embraced by the present invention. When the novel compounds are used as fungicides, both the pure diastereomers or enantiomers and mixtures of these obtained in the synthesis are suitable, the mixtures preferably being used.

X is preferably hydrogen, fluorine, chlorine, bromine, cyano, nitro, trifluoromethyl, methyl, ethyl, n-propyl, isopropyl, n-butyl, isobutyl, sec.-butyl, tert.-butyl, methoxy, ethoxy, methylthio, phenyl or phenoxy.

In formula I, suitable radicals $R^1$ are methyl, ethyl, n-propyl, n-butyl, isobutyl, sec.-butyl, n-pentyl, 3-methylbut-1-yl, 2-methylbut-1-yl, 3-pentyl, n-hexyl, 3,3-dimethylbut-1-yl, 2,2,3-trimethylprop-1-yl, n-heptyl, n-octyl, 2,4,4-trimethylpentyl, 2-ethylhexyl, n-nonyl, 3,5,5-trimethylhexyl, 2-isopropyl-5-methylhexyl, 2-isopropyl-3-methylhexyl, n-decyl, 3,7-dimethyloctyl, dodecyl, cyclopropylmethyl, cyclopentyl, cyclohexyl, cyclohexylmethyl, 4-methylcyclohexyl, 4-tert.-butylcyclohexyl, 4-methoxycyclohexyl, 2-methoxyethyl, 2-ethoxyethyl, 2-propoxyethyl, 2-butoxyethyl, 2-hexyloxyethyl, 3-methoxypropyl, 3-ethoxypropyl, 3-propoxypropyl, 3-butoxypropyl, 3-hexyloxypropyl, 2-methylthioethyl, 2-ethylthioethyl, 2-propylthioethyl, 2-butylthioethyl, 3-methylthiopropyl, 3-ethylthiopropyl, 3-propylthiopropyl, allyl, 2-methylallyl, but-2-en-1-yl, pent-2-en-1-yl, phenyl, 4-fluorophenyl, 4-chlorophenyl, 2,4-dichlorophenyl, 3,4-dichlorophenyl, 4-bromophenyl, 4-methylphenyl, 4-tert.-butylphenyl, 4-methoxyphenyl, 4-ethoxyphenyl, 4-trifluoromethyl, 4-cyanophenyl, benzyl, 4-fluorobenzyl, 4-chlorobenzyl, 3,4-dichlorobenzyl, 2,4-dichlorobenzyl, 4-bromobenzyl, 4-methylbenzyl, 4-tert.-butylbenzyl, 4-methoxybenzyl, 3- and 4-trifluoromethylbenzyl and 4-ethoxybenzyl.

$R^2$ and $R^3$ are each preferably hydrogen, methyl, ethyl, n-propyl or isopropyl, R is methyl or ethyl, Y is nitrogen or CH and m is an integer from 1 to 4.

The compounds of the formula I can be prepared by a method in which a carbamyl chloride of the formula

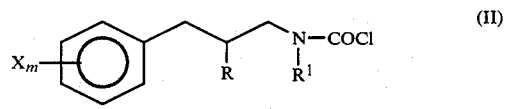

where R, $R^1$ and X have the above meanings, is reacted with (a) an azole of the formula III

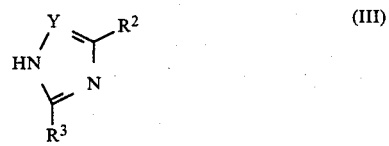

where $R^2$, $R^3$ and Y have the above meanings, or (b) a metal derivative of this, of the formula IV

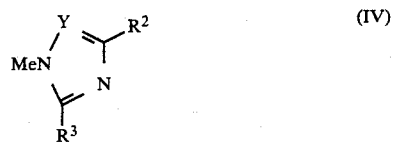

where $R^2$, $R^3$ and Y have the above meanings and Me is lithium, sodium, potassium or an equivalent of calcium, or (c) a silyl derivative of this, of the formula V

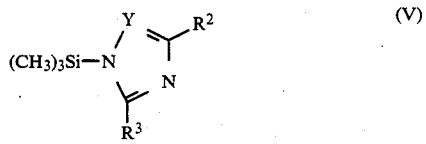

where $R^2$, $R^3$ and Y have the above meanings.

Reaction (a) is carried out in the presence or absence of a solvent or diluent and with or without the addition of an inorganic or organic base and of a reaction accelerator, at from 10° to 120° C.

Examples of preferably used solvents or diluents which are inert to the reactants are aliphatic or aromatic hydrocarbons and halohydrocarbons, such as n-pentane, cyclohexane, methylene chloride, 1,1,1-trichloroethane, benzene, toluene, xylene or chlorobenzene, aliphatic ketones, such as acetone, methyl ethyl ketone or diethyl ketone, ethers, such as diethyl ether, methyl tert.-butyl ether, dimethoxyethane, tetrahydrofuran or dioxane, esters, such as ethyl acetate, nitriles, such as acetonitrile, and amides, such as dimethylformamide, dimethylacetamide and N-methylpyrrolidone, and mixtures of these.

Examples of suitable bases which, if required, may also be used in the reaction as acid acceptors are alkali metal hydroxides, such as lithium hydroxide, sodium hydroxide, potassium hydroxide or calcium hydroxide, alkali metal carbonates, such as sodium carbonate, potassium carbonate, sodium bicarbonate or potassium bicarbonate, and amines, such as triethylamine, tripropylamine, N-methylpyrrolidine, N-methylpiperidine, N,N-dimethylcyclohexylamine, N,N'-tetramethylethylenediamine, N,N-dimethylaniline, N,N-diethylaniline, pyridine or 4-dimethylaminopyridine. Other conventional bases may also be used.

Preferred reaction accelerators are metal halides, such as sodium iodide or potassium iodide, quaternary ammonium salts, such as tetrabutylammonium chloride, bromide or iodide or benzyltriethylammonium chloride or bromide, and crown ethers, such as 12-crown-4, 15-crown-5, 18-crown-6 or dibenzo-18-crown-6.

Reactions (b) and (c) are carried out in the presence or absence of a solvent or diluent, at from 0° to 140° C., preferably from 0° to 100° C. Solvents which can be used for these reactions are those which are suitable for version (a) of the process.

Compounds of the formula I can furthermore be prepared by reacting a secondary amine of the formula VI

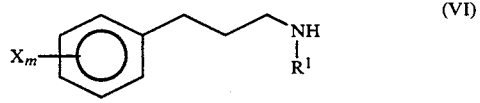

where R, $R^1$ and X have the above meanings, with a carbonyl-bisazole of the formula VII

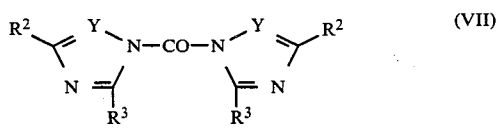

where $R^2$, $R^3$ and Y have the above meanings, in the presence or absence of a solvent or diluent and with or without the addition of a reaction accelerator.

Examples of suitable solvents or diluents for this purpose are diethyl ether, 1,2-dimethoxyethane, dipropyl ether, dibutyl ether, methyl tert.-butyl ether, tetrahydrofuran, dimethoxyethane, anisole, n-pentane, n-hexane, n-heptane, n-octane, isooctane, cyclohexane, toluene, chlorobenzene, xylenes, acetonitrile, ethyl acetate, dimethylformamide, N-methylpyrrolidone, acetone and methyl ethyl ketone.

Examples of suitable reaction accelerators are 4-dimethylaminopyridine and 4-pyrrolidinopyridine.

The starting materials of the formula II can readily be prepared by a conventional method, for example by reacting an amine of the formula VI with phosgene (Houben-Weyl-Muller, Methoden der organischen Chemie, Volume 8, pages 115–118, Georg Thieme Verlag, Stuttgart, 1952).

The secondary amines of the formula VI are obtained by reacting a known amine of the formula $R^1$—$NH_2$, where $R^1$ has the above meanings, with an arylpropyl halide (cf. European Pat. No. 9077) of the formula VIII or with an aldehyde of the formula IX

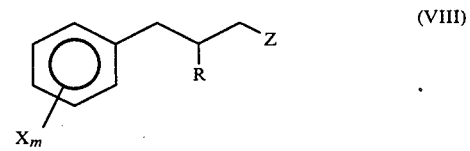

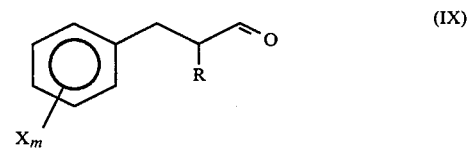

where R, X and m have the above meanings and Z is chlorine or bromine, in the presence or absence of a strong inorganic or organic base, of a solvent or diluent and of a hydrogenating compound and/or a catalyst.

The Examples which follow illustrate the preparation of the compounds of the formula I.

EXAMPLE 1

(a) 204 g of 3-(4'-tert.-butylphenyl)-2-methylpropionaldehyde were added dropwise to a solution of 71 g (1 mole) of n-butylamine in 800 ml of ethanol at 25° C., and the mixture was stirred for 36 hours at 25° C. Thereafter, 87 g (2.28 moles) of sodium borohydride were added, a little at a time, to the mixture, and stirring was continued for a further 4 hours at 78° C. The mixture was cooled, diluted with 1.5 l of water and extracted with three times 300 ml of methylene chloride, and the combined extracts were washed with 300 ml of water, dried and distilled.

170 g of N-butyl-N-(1-(4'-tert.-butylphenyl)-2-methylprop-3-yl)-amine of boiling point 125° C./0.4 mbar were obtained.

(b) 51.2 g (0.196 mole) of N-butyl-N-(1-(4'-tert.-butylphenyl)-2-methylprop-3-yl)-amine were added dropwise to a solution of phosgene in 200 ml of dry ethyl acetate, the solution being saturated at 10° C. The mixture was stirred for 6 hours at 50° C., phosgene being passed in, and then cooled to 20° C. and evaporated down under reduced pressure, in the final stages at 60° C. and under 0.4 mbar.

61 g of N-(1-4'-tert.-butylphenyl)-2-methylprop-3-yl)-N-butylcarbamyl chloride were obtained as a colorless oil, which was directly reacted further.

(c) 20.4 g (0.3 mole) of imidazole were added, a little at a time, to a solution of 32.4 g (0.1 mole) of N-(1-(4'-tert.-butylphenyl)-2-methylprop-3-yl)-N-butylcarbamyl chloride in 250 ml of dry tetrahydrofuran, and the mixture was stirred for 6 hours at 70° C. Thereafter, the mixture was cooled to 20° C., the precipitate formed was filtered off under suction, the filtrate was evaporated down under reduced pressure, the residue was taken up in 200 ml of methylene chloride, and the solution was washed with three times 80 ml of water, dried and evaporated down.

29.2 g of 1-(N-(1-(4'-tert.-butylphenyl)-2-methylprop-3-yl)-N-butylcarbamyl)-imidazole were obtained as a colorless resin (Compound No. 1). IR (film) [$cm^{-1}$]:

2961, 2933, 2872, 1694, 1464, 1421, 1365, 1286, 1272, 1231, 1100, 1066, 1020, 750, 658.

EXAMPLE 2

14 g (0.0433 mole) of N-(1-(4'-tert.-butylphenyl)-2-methylprop-3-yl)-N-butylcarbamyl chloride were added dropwise to a suspension of 5.5 g (0.06 mole) of sodium 1,2,4-triazolide in 120 ml of dry tetrahydrofuran at 20° C., and the mixture was stirred for 6 hours at 65° C. Thereafter, the mixture was cooled to 20° C., the precipitate was filtered off under suction, the filtrate was evaporated down, the residue was dissolved in 150 ml of methylene chloride, and the solution was washed with three times 50 ml of water, dried and evaporated down. 13.3 g of 1-(N-(1-(4'-tert.-butylphenyl)-2-methylprop-3-yl)-N-butylcarbamyl)-1,2,4-triazole were obtained as a colorless resin (Compound No. 2). IR (film) [cm$^{-1}$]: 2961, 2931, 2871, 1699, 1508, 1464, 1426, 1379, 1364, 1275, 1210, 1192, 1136, 1001, 671.

The compounds listed in the Table below can be prepared in a similar manner:

| Compound no. | X | R | R$^1$ | Y | R$^2$ | R$^3$ | M.p. [°C.] IR (film) [cm$^{-1}$] |
|---|---|---|---|---|---|---|---|
| 3 | H | CH$_3$ | n-C$_4$H$_9$ | CH | H | H | |
| 4 | H | CH$_3$ | n-C$_4$H$_9$ | N | H | H | |
| 5 | H | C$_2$H$_5$ | n-C$_4$H$_9$ | CH | H | H | |
| 6 | H | C$_2$H$_5$ | n-C$_4$H$_9$ | N | H | H | |
| 7 | H | CH$_3$ | n-C$_6$H$_{13}$ | CH | H | H | |
| 8 | H | CH$_3$ | n-C$_6$H$_{13}$ | N | H | H | |
| 9 | H | CH$_3$ | cyclopropylmethyl | CH | H | H | |
| 10 | H | CH$_3$ | cyclopropylmethyl | N | H | H | |
| 11 | H | CH$_3$ | —(CH$_2$)$_2$OC$_2$H$_5$ | CH | H | H | |
| 12 | H | CH$_3$ | —(CH$_2$)$_2$OC$_2$H$_5$ | N | H | H | |
| 13 | 4-F | CH$_3$ | n-C$_3$H$_7$ | CH | H | H | 2963, 1692, 1509, 1462, 1421, 1298, 1276, 1242, 1221, 1099, 1013, 760, 656 |
| 14 | 4-F | CH$_3$ | n-C$_3$H$_7$ | N | H | H | 2966, 1699, 1510, 1427, 1220, 1001, 671 |
| 15 | 4-F | CH$_3$ | —(CH$_2$)$_3$OC$_4$H$_5$—n | CH | H | H | |
| 16 | 4-F | CH$_3$ | —(CH$_2$)$_3$O—C$_4$H$_5$—n | N | H | H | |
| 17 | 4-F | CH$_3$ | —C$_6$H$_5$ | CH | H | H | |
| 18 | 4-F | CH$_3$ | —C$_6$H$_5$ | N | H | H | |
| 19 | 4-Cl | CH$_3$ | n-C$_6$H$_{13}$ | CH | H | H | n$_D^{22}$ 1.5342 |
| 20 | 4-Cl | CH$_3$ | n-C$_6$H$_{13}$ | N | H | H | n$_D^{22}$ 1.5279 |
| 21 | 4-Cl | CH$_3$ | —(CH$_2$)$_2$CH(CH$_3$)CH$_2$C(CH$_3$)$_3$ | CH | H | H | |
| 22 | 4-Cl | CH$_3$ | —(CH$_2$)$_2$CH(CH$_3$)CH$_2$C(CH$_3$)$_3$ | N | H | H | |
| 23 | 4-Br | CH$_3$ | n-C$_4$H$_9$ | CH | H | H | |
| 24 | 4-Br | CH$_3$ | n-C$_4$H$_9$ | N | H | H | |
| 25 | 4-CH$_3$O— | CH$_3$ | n-C$_3$H$_7$ | CH | H | H | 2962, 2933, 1692, 1611, 1512, 1462, 1421, 1299, 1275, 1221, 1178, 1034, 754 |
| 26 | 4-CH$_3$O— | CH$_3$ | n-C$_3$H$_7$ | N | H | H | 2963, 1698, 1512, 1426, 1276, 1247, 1179, 1001 |
| 27 | 4-C$_2$H$_5$O— | CH$_3$ | n-C$_6$H$_{13}$ | CH | H | H | |
| 28 | 4-C$_2$H$_5$O— | CH$_3$ | n-C$_6$H$_{13}$ | N | H | H | |
| 29 | 4-C$_6$H$_{13}$O— | CH$_3$ | n-C$_4$H$_9$ | CH | H | H | |
| 30 | 4-C$_6$H$_{13}$O— | CH$_3$ | n-C$_4$H$_9$ | N | H | H | |
| 31 | 4-CH$_3$ | CH$_3$ | n-C$_3$H$_7$ | CH | H | H | 2963, 2930, 1693, 1515, 1461, 1421, 1380, 1364, 1298, 1275, 1220, 1100, 1015, 754 |
| 32 | 4-CH$_3$ | CH$_3$ | n-C$_3$H$_7$ | N | H | H | 2965, 1699, 1428, 1381, 1275, 1138, 1001, 748 |
| 33 | 4-C$_2$H$_5$ | CH$_3$ | n-C$_6$H$_{13}$ | CH | H | H | |
| 34 | 4-C$_2$H$_5$ | CH$_3$ | n-C$_5$H$_{13}$ | N | H | H | |
| 35 | 4-isoC$_3$H$_7$ | CH$_3$ | n-C$_4$H$_9$ | CH | H | H | |
| 36 | 4-isoC$_3$H$_7$ | CH$_3$ | n-C$_4$H$_9$ | N | H | H | |
| 37 | 4-isoC$_3$H$_7$ | CH$_3$ | n-C$_6$H$_{13}$ | CH | H | H | |
| 38 | 4-isoC$_3$H$_7$ | CH$_3$ | n-C$_6$H$_{13}$ | N | H | H | |
| 39 | 4-tert.-C$_4$H$_9$ | CH$_3$ | CH$_3$ | CH | H | H | 70-72 |
| 40 | 4-tert.-C$_4$H$_9$ | CH$_3$ | CH$_3$ | CH | H | isoC$_3$H$_7$ | 2965, 2931, 2870, 1701, 1510, 1476, 1461, 1364, 1244, 1231, 1108 |
| 41 | 4-tert.-C$_4$H$_9$ | CH$_3$ | CH$_3$ | N | H | H | 2961, 2869, 1704, 1508, 1478, 1406, 1380, 1364, 1275, 1197, 1131, 998, 746, 671 |
| 42 | 4-tert.-C$_4$H$_9$ | CH$_3$ | C$_2$H$_5$ | CH | H | H | 2963, 1695, 1461, 1422, 1328, 1249, 1220, 1018, 900, 758 |
| 43 | 4-tert.-C$_4$H$_9$ | CH$_3$ | C$_2$H$_5$ | N | H | H | |
| 44 | 4-tert.-C$_4$H$_9$ | CH$_3$ | n-C$_3$H$_7$ | CH | H | H | 2963, 2873, 1693, 1462, 1420, 1365, 1272, 1242, 1100, |

-continued

| Compound no. | X | R | R¹ | Y | R² | R³ | M.p. [°C.] IR (film) [cm⁻¹] |
|---|---|---|---|---|---|---|---|
| 45 | 4-tert.-C₄H₉ | CH₃ | n-C₃H₇ | CH | H | iso-C₃H₇ | 1065, 1017, 755, 658 2964, 2872, 1693, 1511, 1460, 1417, 1380, 1363, 1346, 1269, 1109, 1096, 1070 |
| 46 | 4-tert.-C₄H₉ | CH₃ | n-C₃H₇ | N | H | H | 2963, 2873, 1700, 1509, 1462, 1426, 1380, 1364, 1274, 1244, 1211, 1001, 671 |
| 47 | 4-tert.-C₄H₉ | CH₃ | n-C₄H₉ | CH | H | isoC₃H₇ | 2962, 2872, 1695, 1460, 1418, 1379, 1363, 1288, 1270, 1109, 1096, 1070, 718 |
| 48 | 4-tert.-C₄H₉ | CH₃ | —(CH₂)₂CH(CH₃)₂ | CH | H | H |  |
| 49 | 4-tert.-C₄H₉ | CH₃ | —(CH₂)₂CH(CH₃)₂ | N | H | H |  |
| 50 | 4-tert.-C₄H₉ | CH₃ | n-C₆H₁₃ | CH | H | H | $n_D^{23}$ 1.5205 |
| 51 | 4-tert.-C₄H₉ | CH₃ | n-C₆H₁₃ | N | H | H |  |
| 52 | 4-tert.-C₄H₉ | CH₃ | —CH₂CH(C₂H₅)(CH₂)₃CH₃ | CH | H | H |  |
| 53 | 4-tert.-C₄H₉ | CH₃ | —CH₂CH(C₂H₅)(CH₂)₃CH₃ | N | H | H |  |
| 54 | 4-tert.-C₄H₉ | CH₃ | n-C₇H₁₅ | CH | H | H |  |
| 55 | 4-tert.-C₄H₉ | CH₃ | n-C₇H₁₅ | N | H | H |  |
| 56 | 4-tert.-C₄H₉ | CH₃ | 4-Cl-C₆H₄— | CH | H | H | 1701, 1494, 1416, 1394, 1287, 1251, 1095, 1015, 846, 750, 735, 654, 570 |
| 57 | 4-tert.-C₄H₉ | CH₃ | 4-Cl-C₆H₄— | CH | H | isoC₃H₇ | 1701, 1493, 1414, 1393, 1289, 1269, 1095, 1070, 1016, 838, 759, 738, 723, 608 |
| 58 | 4-tert.-C₄H₉ | CH₃ | 4-Cl—C₆H₄— | N | H | H | 1708, 1509, 1493, 1458, 1440, 1420, 1400, 1380, 1281, 1092, 1014, 990 |
| 59 | 4-tert.-C₄H₉ | CH₃ | cyclohexyl | CH | H | H |  |
| 60 | 4-tert.-C₄H₉ | CH₃ | cyclohexyl | N | H | H | 2933, 1700, 1508, 1421, 1273, 1003, 731, 671 |
| 61 | 4-tert.-C₄H₉ | CH₃ | 4-methylcyclohexyl | CH | H | H | 2858, 1695, 1410, 1240, 1100, 1019, 732, 657 |
| 62 | 4-tert.-C₄H₉ | CH₃ | 4-methylcyclohexyl | N | H | H |  |
| 63 | 4-C(CH₃)₂C₂H₅ | CH₃ | n-C₆H₁₃ | CH | H | H | $n_D^{22}$ 1.5168 |
| 64 | 4-C(CH₃)₂C₂H₅ | CH₃ | n-C₆H₁₃ | N | H | H | $n_D^{22}$ 1.5111 |
| 65 | 4-CF₃ | CH₃ | n-C₆H₁₃ | CH | H | H |  |
| 66 | 4-CF₃ | CH₃ | n-C₆H₁₃ | N | H | H |  |
| 67 | 4-isoC₃H₇ | CH₃ | CH₃ | CH | H | H | 2959, 2927, 1696, 1512, 1484, 1459, 1402, 1382, 1282, 1217, 1099, 1009, 754, 656 |
| 68 | 4-iso-C₃H₇ | CH₃ | CH₃ | N | H | H | 2959, 2927, 1703, 1510, 1479, 1406, 1381, 1363, 1276, 1198, 1131, 998, 671 |
| 69 | 2,4-Cl₂ | CH | n-C₃H₇ | CH | H | H | 2963, 2933, 1693, 1473, 1420, 1382, 1299, 1275, 1242, 1103, 1066, 1015, 744, 657 |
| 70 | 2,4-Cl₂ | CH₃ | n-C₃H₇ | N | H | H | 2965, 1698, 1474, 1426, 1382, 1276, 1244, 1105, 1001, 746, 670 |
| 71 | 2,4-Cl₂ | CH₃ | —CH₂—CH=CH₂ | CH | H | H |  |
| 72 | 2,4-Cl₂ | CH₃ | —CH₂—CH=CH₂ | N | H | H |  |
| 73 | 2,4-Cl₂ | CH₃ | —CH₂—CH=CH—CH₃ | CH | H | H |  |
| 74 | 2,4-Cl₂ | CH₃ | —CH₂—CH=CH—CH₃ | N | H | H |  |
| 75 | 2,4-Cl₂ | CH₃ | —CH₂—CH=CH—C₃H₆ | CH | H | H |  |
| 76 | 2,4-Cl₂ | CH₃ | iso-C₄H₉ | CH | H | H | 2960, 1693, 1472, 1419, 1385, 1277, 1244, 1103, 1065, 1018, 745, 657 |
| 77 | 2,4-Cl₂ | CH₃ | iso-C₄H₉ | N | H | H | 2961, 1698, 1473, 1381, 1275, 1003, 670 |
| 78 | 2,4-Cl₂ | CH₃ | n-C₁₂H₂₅ | CH | H | H | 2953, 2924, 2853, 1695, 1472, 1420, 1379, 1299, 1274, 1240, 1220, 1103, 1065, 744 |
| 79 | 2,4-Cl₂ | CH₃ | n-C₁₂H₂₅ | N | H | H | 2924, 1699, 1472, 1426, |

-continued

| Compound no. | X | R | R¹ | Y | R² | R³ | M.p. [°C.] IR (film) [cm$^{-1}$] |
|---|---|---|---|---|---|---|---|
| 80 | 2,4-Cl$_2$ | CH$_3$ | cyclohexyl | CH | H | H | 1275, 1000, 744, 670 2933, 1694, 1474, 1409, 1377, 1303, 1240, 1103, 1020, 746 |
| 81 | 2,4-Cl$_2$ | CH$_3$ | cyclohexyl | N | H | H | 65–67 |
| 82 | H | n-C$_3$H$_7$ | n-C$_6$H$_{13}$ | CH | H | H | n$_D^{25}$ 1.5321 |
| 83 | H | n-C$_3$H$_7$ | n-C$_6$H$_{13}$ | N | H | H | n$_D^{25}$ 1.5136 |
| 84 | H | n-C$_4$H$_9$ | n-C$_4$H$_9$ | CH | H | H | n$_D^{22}$ 1.5224 |
| 85 | H | n-C$_4$H$_9$ | n-C$_4$H$_9$ | N | H | H | n$_D^{22}$ 1.5172 |
| 86 | H | n-C$_4$H$_9$ | n-C$_6$H$_{13}$ | CH | H | H | n$_D^{20}$ 1.5178 |
| 87 | H | n-C$_4$H$_9$ | n-C$_6$H$_{13}$ | N | H | H | n$_D^{20}$ 1.5125 |
| 88 | 2-F | CH$_3$ | n-C$_4$H$_9$ | CH | H | H | n$_D^{22}$ 1.5262 |
| 89 | 2-F | CH$_3$ | n-C$_4$H$_9$ | NH | H | H | n$_D^{22}$ 1.5180 |
| 90 | 2-F | CH$_3$ | n-C$_6$H$_{13}$ | CH | H | H | n$_D^{22}$ 1.5192 |
| 91 | 4-Cl | CH$_3$ | n-C$_4$H$_9$ | CH | H | H | n$_D^{23}$ 1.5428 |
| 92 | 4-CH$_3$ | CH$_3$ | cyclohexyl | CH | H | H | 2930, 1694, 1515, 1409, 1376, 1241, 1100, 1020, 757 |
| 93 | 4-CH$_3$ | CH$_3$ | cyclohexyl | N | H | H | 2931, 1700, 1507, 1422, 1378, 1274, 1178, 1003, 671 |
| 94 | 4-C(CH$_3$)$_3$ | CH$_3$ | n-C$_4$H$_9$ | CH | H | H | 2959, 1694, 1420, 1364, 1271, 1230, 1020, 656, 671 |
| 95 | 4-C(CH$_3$)$_3$ | CH$_3$ | n-C$_4$H$_9$ | N | H | H | 2960, 1699, 1426, 1379, 1274, 1210, 1001, 671 |
| 96 | 4-C(CH$_3$)$_3$ | CH$_3$ | n-C$_8$H$_{17}$ | CH | H | H | n$_D^{25}$ 1.5158 |
| 97 | 4-C(CH$_3$)$_3$ | CH$_3$ | n-C$_8$H$_{17}$ | N | H | H | n$_D^{22}$ 1.5096 |
| 98 | 4-C(CH$_3$)$_3$ | CH$_3$ | n-C$_5$H$_{11}$ | CH | H | H | n$_D^{23}$ 1.5176 |
| 99 | 4-C(CH$_3$)$_3$ | CH$_3$ | n-C$_5$H$_{11}$ | N | H | H | n$_D^{23}$ 1.5135 |
| 100 | 4-C(CH$_3$)$_3$ | CH$_3$ | —HC(CH$_3$)CH$_2$CH$_2$CH$_3$ | CH | H | H | n$_D^{23}$ 1.5268 |
| 101 | 4-C(CH$_3$)$_3$ | CH$_3$ | —HC(CH$_3$)CH$_2$CH$_2$CH$_3$ | N | H | H | n$_D^{23}$ 1.5192 |
| 102 | 4-C(CH$_3$)$_3$ | CH$_3$ | iso-C$_4$H$_9$ | CH | H | H | n$_D^{22}$ 1.5190 |
| 103 | 4-C(CH$_3$)$_3$ | CH$_3$ | iso-C$_4$H$_9$ | N | H | H | 2960, 1694, 1419, 1267, 1244, 1099, 1018, 804 |
| 104 | 4-C(CH$_3$)$_3$ | CH$_3$ | (CH$_3$)$_2$CHCH$_2$CH$_2$— | CH | H | H | n$_D^{23}$ 1.5215 |
| 105 | 4-C(CH$_3$)$_3$ | CH$_3$ | —HC(CH$_3$)C$_5$H$_{11}$—n | CH | H | H | 2960, 1694, 1408, 1375, 1325, 1298, 1099, 759 |
| 106 | 4-C(CH$_3$)$_2$C$_2$H$_5$ | CH$_3$ | n-C$_4$H$_9$ | CH | H | H | n$_D^{20}$ 1.5242 |
| 107 | 4-C(CH$_3$)$_2$C$_2$H$_5$ | CH$_3$ | n-C$_4$H$_9$ | N | H | H | n$_D^{22}$ 1.5183 |
| 108 | 4-C(CH$_3$)$_2$C$_2$H$_5$ | CH$_3$ | n-C$_6$H$_{13}$ | CH | H | H | n$_D^{25}$ 1.5194 |
| 109 | 4-C(CH$_3$)$_2$C$_2$H$_5$ | CH$_3$ | n-C$_6$H$_{13}$ | N | H | H | n$_D^{25}$ 1.5146 |
| 110 | 4-C(CH$_3$)$_2$C$_3$H$_7$n | CH$_3$ | n-C$_4$H$_9$ | CH | H | H | n$_D^{25}$ 1.5221 |
| 111 | 4-C(CH$_3$)$_2$C$_3$H$_7$n | CH$_3$ | n-C$_4$H$_9$ | N | H | H | n$_D^{25}$ 1.5172 |
| 112 | 4-C(CH$_3$)$_2$C$_3$H$_7$n | CH$_3$ | n-C$_4$H$_{13}$ | CH | H | H | n$_D^{23}$ 1.5154 |
| 113 | 4-C(CH$_3$)$_2$C$_3$H$_7$-i | CH$_3$ | n-C$_4$H$_9$ | CH | H | H | n$_D^{26}$ 1.5176 |
| 114 | 4-C(CH$_3$)$_2$C$_3$H$_7$-i | CH$_3$ | n-C$_4$H$_9$ | N | H | H | n$_D^{26}$ 1.5187 |
| 115 | 4-C(CH$_3$)$_2$C$_3$H$_7$-i | CH$_3$ | n-C$_6$H$_{13}$ | CH | H | H | n$_D^{22}$ 1.5222 |

The novel compounds have an excellent action on a broad spectrum of plant-pathogenic fungi, especially from the Ascomycetes and Basidiomycetes classes. Some of them have a systemic action and may be used as soil or foliar herbicides. They may also be used for protecting materials, inter alia for combatting wood-destroying fungi such as *Coniophora puteana* and *Polystictus versicolor*. The novel active ingredients also effectively combat molds and wood-discoloring fungi such as *Pullularia pullulans*. Further, the novel compounds are effective on *Candida albicans* and *Trichophyton mentographytes*.

The fungicidal compounds are of particular interest for combatting a large number of fungi in various crops or their seed, especially wheat, rye, barley, oats, rice, Indian corn, cotton, soybeans, coffee, sugarcane, fruit, ornamentals in horticulture, and vegetables, such as cucumbers, beans and Cucurbitaceae.

The novel compounds are particularly suitable for combatting the following diseases: *Pseudocercosporella herpotrichoides* in cereals, *Erysiphe graminis* in cereals, *Erysiphe cichoriacearum* in Cucurbitaceae, *Podosphaera leucotricha* in apples, *Uncinula necator* in grapes, *Puccinia* species in cereals, *Rhizoctonia solani* in cotton, *Ustilago* species in cereals and sugarcane, *Venturia inaequalis* (scab) in apples, *Septoria nodorum* in wheat, *Botrytis cinerea* in strawberries and grapes, and *Rhynchosporium secalis* and *Pyrenophora teres* in cereals.

The active ingredients may simultaneously suppress the growth of two or more of the said fungi, and are excellently tolerated by plants. Some of the active ingredients also have curative properties, i.e., the agents may be applied after infection of the plants by the pathogen and success is still ensured.

The fungicidal agents contain from 0.1 to 95, and preferably from 0.5 to 90, wt% of active ingredient. The application rates depend on the type of effect desired, and range from 0.1 to 5 kg of active ingredient per hectare.

The novel active ingredients may also be mixed and applied with other active ingredients, e.g., herbicides, insecticides, growth regulators, other fungicides and fertilizers. When mixed with other fungicides, the spectrum of fungicidal action is in many cases increased;

with a number of these fungicidal compositions, synergistic effects also occur, i.e., the fungicidal action of the combination product is greater than the effect of the individual components added together. Examples of fungicides which can be combined with the novel compounds are as follows:

sulfur
dithiocarbamates and derivatives thereof, such as
ferric dimethyldithiocarbamate
zinc dimethyldithiocarbamate
zinc ethylenebisthiocarbamate
tetramethylthiuram disulfide
manganese ethylene bis-dithiocarbamate
manganese-zinc ethylenediamine-bisdithiocarbamate
ammonia complex of zinc-(N,N'-ethylene)-bisdithiocarbamate and
N,N'-polyethylene-bis-(thiocarbamoyl)-disulfide
ammonia complex of zinc-(N,N'-propylene-bisdithiocarbamate) and
N,N'-polypropylene-bis-(thiocarbamoyl)-disulfide
nitro derivatives, such as
dinitro-(1-methylheptyl)-phenylcrotonate
2-sec-butyl-4,6-dinitrophenyl-3,5-dimethylacrylate
2-sec-butyl-4,6-dinitrophenylisopropylcarbonate
diisopropyl 5-nitroisophthalate
heterocyclic structures, such as
2-heptadecyl-2-imidazoline acetate
2,4-dichloro-6-(o-chloroanilino)-s-triazine
O,O-diethylphthalimidophosphorothionate
5-amino-1-[bis-(dimethylamino)-phosphynyl]-3-phenyl-1,2,4-triazole
2,3-dicyano-1,4-dithiaanthraquinone
2-thio-1,3-dithio-(4,5-b)-quinoxaline
methyl 1-(butylcarbamoyl)-2-benzimidazole carbamate
2-methoxycarbonylaminobenzimidazole
2-[furyl-(2)]-benzimidazole
2-[thiazolyl-(4)]-benzimidazole
N-(1,1,2,2-tetrachloroethylthio)-tetrahydrophthalimide
N-trichloromethylthiotetrahydrophthalimide
N-trichloromethylphthalamide
N-dichlorofluoromethylthio-N',N'-dimethyl-N-phenyl-sulfuric acid diamide
5-ethoxy-3-trichloromethyl-1,2,3-thiadiazole
2-thiocyanomethylthiobenzthiazole
1,4-dichloro-2,5-dimethoxybenzole
4-(2-chlorophenylhydrazono)-3-methyl-5-isoxazolone
pyridine-2-thio-1-oxide
8-hydroxyquinoline and its copper salt
2,3-dihydro-5-carboxanilido-6-methyl-1,4-oxathiyne-4,4-dioxide
2,3-dihydro-5-carboxanilido-6-methyl-1,4-oxathiyne
2-methyl-5,6-dihydro-4-H-pyran-3-carboxanilide
2-methyl-furan-3-carboxanilide
2,5-dimethyl-furan-3-carboxanilide
2,4,5-trimethyl-furan-3-carboxanilide
2,5-dimethyl-furan-3-carboxylic acid cyclohexylamide
N-cyclohexyl-N-methoxy-2,5-dimethyl-furan-3-carboxamide
2-methyl-benzoic acid anilide
2iodobenzoic anilide
N-formyl-N-morpholine-2,2,2-trichloroethylacetal
piperazine-1,4-diylbis-(1-(2,2,2-trichloroethyl)-formamide
1-(3,4-dichloroanilino)-1-formylamino-2,2,2-trichloroethane
2,6-dimethyl-N-tridecyl-morpholine and its salts
2,6-dimethyl-N-cyclododecyl-morpholine and its salts
N-[3-(p-tert.-butylphenyl)-2-methylpropyl]-cis-2,6-dimethylmorpholine
N-[3-(p-tert.-butylphenyl)-2-methylpropyl]-piperidine
1-[2-(2,4-dichlorophenyl)-4-ethyl-1,3-dioxolan-2-yl-ethyl]-1-H-1,2,4-triazole
1-[2-(2,4-dichlorophenyl)-4-n-propyl-1,3-dioxolan-2-yl-ethyl]-1-H-1,2,4-triazole
N-(n-propyl)-N-(2,4,6-trichlorophenoxyethyl)-N'-imidazol-ylurea
1-(4-chlorophenoxy)-3,3-dimethyl-1-(1H-1,2,4-triazol-1-yl)-2-butanone
1-(4-chlorophenoxy)-3,3-dimethyl-1-(1H-1,2,4-triazol-1-yl)-2-butanol
alpha-(2-chlorophenyl)-alpha-(4-chlorophenyl)-5-pyrimidinemethanol
5-butyl-2-dimethylamino-4-hydroxy-6-methylpyrimidine
bis-(p-chlorophenyl)-3-pyridinemethanol
1,2-bis-(3-ethoxycarbonyl-2-thioureido)-benzene
1,2-bis-(3-methoxycarbonyl)-2-thioureido)-benzene
and various fungicides, such as
dodecylguanidine acetate
3-[2-(3,5-dimethyl-2-oxycyclohexyl)-2-hydroxyethyl]-glutarimide
hexachlorobenzene
D,L-methyl-N-(2,6-dimethylphenyl)-N-(2-furoyl)-alanate
methyl D,L-N-(2,6-dimethylphenyl)-N-(2-methoxyacetyl)-alanate
N-(2,6-dimethylphenyl)-N-chloroacetyl-D,L-2-aminobutyrolactone
methyl DL-N-(2,6-dimethylphenyl)-N-(phenylacetyl)-alanate
5-methyl-5-vinyl-3-(3,5-dichlorophenyl)-2,4-dioxo-1,3-oxazolidine
3-(3,5-dichlorophenyl)-5-methyl-5-methoxymethyl-1,3-oxazolidine-2,4-dione
3-(3,5-dichlorophenyl)-1-isopropyl-carbamoylhydantoin
N-(3,5-dichlorophenyl)-1,2-dimethyl-cyclopropane-1,2-dicarboximide
2-cyano-N-(ethylaminocarbonyl)-2-(methoximino)-acetamide
1-(2-(2,4-dichlorophenyl)-pentyl)-1H-1,2,4-triazole
2,3-difluoro-alpha-(1H-1,2,4-triazol-1-ylmethyl)-benzhydryl alcohol.

The novel active ingredients are applied for instance in the form of directly sprayable solutions, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used, but they must ensure as fine a distribution of the novel active ingredients as possible.

For the preparation of solutions, emulsions, pastes and oil dispersions to be used direct or after emulsification in water, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, and N-methylpyrrolidone, and water are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkyl-aryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus day, limestone, lime, chalk, bole, loess, clay, dolomite, diatomaceous earth, calcium sulfate, magnesium sulfate, magnesium oxide, ground plastics, fertilizers such as ammonium sulfates, ammonium phosphate, ammonium nitrate, and ureas, and vegetable products such as grain flours, bark meal, wood meal, and nutshell meal, cellulosic powders, etc.

Examples of such formulations are given below.

I. 90 parts by weight of compound 1 is mixed with 100 parts by weight of N-methyl-alpha-pyrrolidone. A mixture is obtained which is suitable for application in the form of very fine drops.

II. 20 parts by weight of compound 25 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of the compound obtainable in accordance with Example 39 is dissolved in a mixture consisting of 30 parts by weight of cyclohexanone, 30 parts by weight of isobutanol, and 20 parts by weight of the adduct of 40 moles of ethylene oxide and 1 mole of castor oil. By pouring the solution into water and finely distributing it therein, an aqueous dispersion is obtained.

IV. 20 parts by weight of compound 44 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 20 parts by weight of compound 80 is well mixed with 3 parts by weight of the sodium salt of diisobutylnaphthalene-alpha-sulfonic acid, 17 parts by weight of the sodium salt of a lignin-sulfonic acid obtained from a sulfite waste liquor, and 60 parts by weight of powdered silica gel, and triturated in a hammer mill. By uniformly distributing the mixture in water, a spray liquor is obtained.

VI. 5 parts by weight of the compound obtainable in accordance with Example 40 is intimately mixed with 95 parts by weight of particulate kaolin. A dust is obtained containing 5% by weight of the active ingredient.

VII. 30 parts by weight of compound 76 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 41 is intimately mixed with 30 parts of the sodium salt of a phenolsulfonic acid-urea-formaldehyde condensate, 2 parts of silica gel and 48 parts of water to give a stable aqueous dispersion.

IX. 20 parts of compound 46 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The following experiments demonstrate the biological action of the novel compounds. The agents used for comparison purposes were the prior art active ingredients N-trichloromethylthiotetrahydrophthalimide (A) and N-trichloromethylthiophthalamide (B) particularly suitable for combatting Botrytis.

EXPERIMENT 1

Action on *Botrytis cinerea* in pimientos

Pimiento seedlings of the "Neusiedler Ideal Elite" variety were sprayed, after 4 to 5 leaves were well developed, to runoff with aqueous suspensions contaning (dry basis) 80% of active ingredient and 20% of emulsifier. After the sprayed-on layer had dried, the plants were sprinkled with a conidial suspension of the fungus *Botrytis cinerea,* and placed at 22° to 24° C. in a chamber of high humidity. After 5 days, the disease had spread to such a great extent on the untreated plants that the necroses covered the major portion of the leaves.

The results of this experiment show that for instance compounds nos. 1, 25, 39, 44 and 80, applied as 0.05% spray liquors, had a better fungicidal action (e.g., 90%) than prior art active ingredient A (e.g., 70%).

EXPERIMENT 2

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 10 days in the greenhouse. Then the leaves were infected with a zoospore suspension of *Plasmopara viticola*. The plants were first placed for 16 hours in a water vapor-saturated chamber at 24° C. and then in a greenhouse for 8 days at from 20° to 30° C. To accelerate and intensify the sporangiophore discharge, the plants were then again placed in the moist chamber for 16 hours. The extent of fungus attack was then assessed on the undersides of the leaves.

The results of the experiment show that for instance compounds nos. 40, 44 and 76, applied as 0.05% spray liquors, had a better fungicidal action (e.g., 97%) than prior art active ingredient B (e.g., 90%).

EXPERIMENT 3

Action on *Pyricularia oryzae* (protective)

Leaves of pot-grown rice seedlings of the "Bahia" variety were sprayed to runoff with aqueous emulsions consisting (dry basis) of 80% of active ingredient and 20% of emulsifier, and inoculated 24 hours later with an aqueous spore suspension of *Pyricularia oryzae*. The plants were then set up in climatic cabinets at 22° to 24° C. and a relative humidity of 95 to 99%. The extent of fungus spread was determined after 6 days.

The results of this experiment show that for example compounds nos. 2, 40, 41, 46, 58, 67, 68, 69 and 70, applied as 0.05% spray liquors, had a good fungicidal action (e.g., 97%).

We claim:

1. An N-(arylpropyl)-azolylurea of the formula

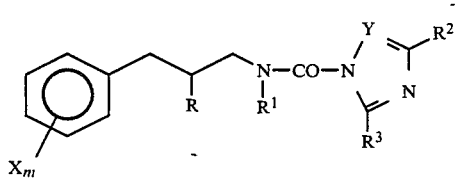

where R is alkyl of 1 to 4 carbon atoms, X is hydrogen, halogen, nitro, cyano, trifluoromethyl or alkyl, alkoxy or alkylthio, each of which is of 1 to 6 carbon atoms, or phenyl or phenoxy, m is an integer from 1 to 4, the individual groups X being identical or different when m is greater than 1, Y is CH or N, $R^1$ is alkyl, alkenyl, alkoxyalkyl, alkylthioalkyl, cycloalkyl or cycloalkylalkyl, each of not more than 12 carbon atoms, 4-methylcyclohexyl, 4-tert.-butylcyclohexyl or 4-methoxycyclohexyl or is phenyl or benzyl, each of which is unsubstituted or substituted by halogen, $C_1$–$C_2$-alkyl, $C_1$–$C_4$-alkoxy, trifluoromethyl, nitro or cyano, and $R^2$ and $R^3$ are identical or different and are each hydrogen or alkyl of 1 to 5 carbon atoms.

2. An N-(arylpropyl)-azolylurea of the formula I as set forth in claim 1, where X is hydrogen, fluorine, chlorine, bromine, cyano, nitro, trifluoromethyl, methyl, ethyl, n-propyl, isopropyl, n-butyl, isobutyl, sec-butyl, tert-butyl, methoxy, ethoxy, methylthio, phenyl or phenoxy, R is methyl or ethyl, $R^2$ and $R^3$ are hydrogen, methyl, ethyl, n-propyl or isopropyl, Y is CH or nitrogen, and $R^1$ is methyl, ethyl, n-propyl, n-butyl, isobutyl, sec.-butyl, n-pentyl, 3-methylbut-1-yl, 2-methylbut-1-yl, 3-pentyl, n-hexyl, 3,3-dimethylbut-1-yl, 2,2,3-trimethylprop-1-yl, n-heptyl, n-octyl, 2,4,4-trimethylpentyl, 2-ethylhexyl, n-nonyl, 3,5,5-trimethylhexyl, 2-isopropyl-5-methylhexyl, 2-isopropyl-3-methylhexyl, n-decyl, 3,7-dimethyloctyl, dodecyl, cyclopropylmethyl, cyclopentyl, cyclohexyl, cyclohexylmethyl, 4-methylcyclohexyl, 2-methoxyethyl, 2-ethoxyethyl, 2-propoxyethyl, 2-butoxyethyl, 3-methoxypropyl, 3-ethoxypropyl, 3-propoxypropyl, 3-butoxypropyl, 2-methylthioethyl, 2-ethylthioethyl, 3-methylthiopropyl, allyl, but-2-en-1-yl, pent-2-en-1-yl, phenyl, p-chlorophenyl, p-methoxyphenyl, p-methylphenyl, benzyl, p-chlorobenzyl, 2,4-dichlorobenzyl, p-methylbenzyl or phenylethyl, and m is an integer from 1 to 4.

3. A process for combatting fungi, wherein the fungi or the materials, areas, plants or seed threatened by fungus attack are treated with a fungicidally effective amount of an N-(arylpropyl)-azolylurea of the formula

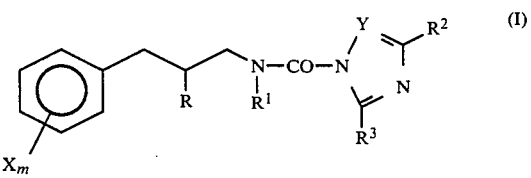

where R is alkyl of 1 to 4 carbon atoms, X is hydrogen, halogen, nitro, cyano, trifluoromethyl or alkyl, alkoxy or alkylthio, each of which is of 1 to 6 carbon atoms, or phenyl or phenoxy, m is an integer from 1 to 4, the individual groups X being identical or different when m is greater than 1, Y is CH or N, $R^1$ is alkyl, alkenyl, alkoxyalkyl, alkylthioalkyl, cycloalkyl or cycloalkylalkyl, each of not more than 12 carbon atoms, 4-methylcyclohexyl, 4-tert.-butylcyclohexyl or 4-methoxycyclohexyl or is phenyl or benzyl, each of which is unsubstituted or substituted by halogen, $C_1$–$C_4$-alkyl, $C_1$–$C_4$-alkoxy, trifluoromethyl, nitro or cyano, and $R^2$ and $R^3$ are identical or different and are each hydrogen or alkyl of 1 to 5 carbon atoms.

4. A fungicidal agent containing an inert additive and an N-(arylpropyl)-azolylurea of the formula

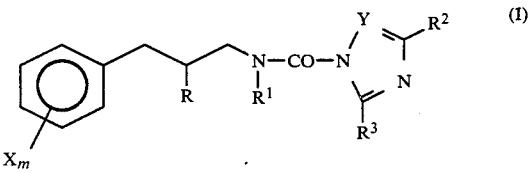

where R is alkyl of 1 to 4 carbon atoms, X is hydrogen, halogen, nitro, cyano, trifluoromethyl or alkyl, alkoxy or alkylthio, each of which is of 1 to 6 carbon atoms, or phenyl or phenoxy, m is an integer from 1 to 4, the individual groups X being identical or different when m is greater than 1, Y is CH or N, $R^1$ is alkyl, alkenyl, alkoxyalkyl, alkylthioalkyl, cycloalkyl or cycloalkylalkyl, each of not more than 12 carbon atoms, 4-methylcyclohexyl, 4-tert.-butylcyclohexyl or 4-methoxycyclohexyl, or is phenyl or benzyl, each of which is unsubstituted or substituted by halogen, $C_1$–$C_4$-alkyl, $C_1$–$C_4$-alkoxy, trifluoromethyl, nitro or cyano, and $R^2$ and $R^3$ are identical or different and are each hydrogen or alkyl of 1 to 5 carbon atoms.

* * * * *